Figure 1:
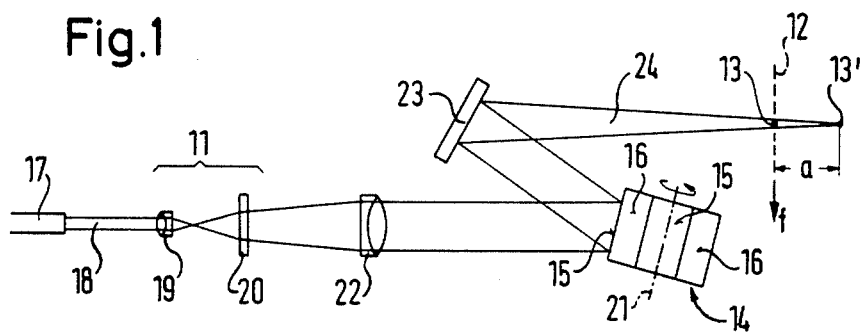

United States Patent [19]

Mankel et al.

[11] 4,357,071

[45] Nov. 2, 1982

[54] OPTICAL FAULT SEEKING APPARATUS

[75] Inventors: Siegfried Mankel, Geretsried; Klaus Ostertag, Munich; Heinz Schreyer, Puchheim, all of Fed. Rep. of Germany

[73] Assignee: Erwin Sick GmbH, Optik-Elektronic, Waldkirch, Fed. Rep. of Germany

[21] Appl. No.: 138,034

[22] Filed: Apr. 7, 1980

[30] Foreign Application Priority Data

Jun. 26, 1979 [DE] Fed. Rep. of Germany ....... 2925734

[51] Int. Cl.³ ............................................. G01N 21/86
[52] U.S. Cl. .................................. 350/6.8; 250/572; 356/431
[58] Field of Search ................... 350/6.5, 6.6, 6.7, 6.8, 350/6.9; 358/199, 139; 356/431, 430, 429; 250/572, 563

[56] References Cited

U.S. PATENT DOCUMENTS

| | | | |
|---|---|---|---|
| 3,488,102 | 1/1970 | Buck et al. | 350/6.8 |
| 4,005,926 | 2/1977 | Neale et al. | 350/6.8 |
| 4,116,566 | 9/1978 | Sick | 350/6.7 |
| 4,123,134 | 10/1978 | Meyers | 350/6.7 |
| 4,265,545 | 5/1981 | Slaker | 356/431 |
| 4,277,178 | 7/1981 | Cushing et al. | 356/431 |

Primary Examiner—R. A. Rosenberger
Attorney, Agent, or Firm—Townsend and Townsend

[57] ABSTRACT

Optical fault seeking apparatus for material webs uses an optical scanning device to scan the material webs point by point line by line. The optical scanning device consists of a laser light source (17) which projects a light beam via a micro-objective (19), a cylindrical lens (20), and a further objective onto a mirror wheel arrangement (14) which is located substantially at the focus of a strip-like concave mirror (23). A light beam (24) is produced in the image space of the strip-like concave mirror (23) and generates a scanning light bead in a scanning plane through which the material web passes. The mirror wheel arrangement (14) has at least first and second alternately operating types of mirror surfaces which serve to alternately project light beads of different size and/or shape onto the material web thus enabling different types of fault to be reliably detected. The different types of scanning light bead are produced either by different curvatures of the faces (15) and (17) of the mirror wheel arrangement (14) or by the use of other optical means alone or in combination with differently shaped faces of the mirror wheel. Certain embodiments operate using two mirror wheels in tandem.

18 Claims, 7 Drawing Figures

OPTICAL FAULT SEEKING APPARATUS

The invention relates to optical fault seeking apparatus for material webs and has particular reference to fault seeking apparatus of the kind in which an optical scanning device including mirror wheel means and a laser is used to generate a scanning light beam and to project the scanning light beam onto the web. In apparatus of this kind the scanning light beam cyclically scans the material web, which is arranged to move past the scanning device, transversely to its length and one or more light receiving devices pick up light reflected from the web and/or passing through the web. The, or each, light receiving device includes at least one photoelectric converter which produces an electrical signal corresponding to the light received. The presence of, absence of, or variations in the signals provide information as to the presence and nature of a fault in the material web.

Optical fault seeking apparatus of this kind consists essentially of a laser light source, an objective and a mirror wheel arranged at the focal point of a strip-like concave mirror. The mirror wheel periodically scans the light beam received from the objective over the concave mirror from which there emerges the scanning light beam which is continuously displaced parallel to itself and which is directed towards the scanning plane in which the material web is moved in its longitudinal direction. The scanning of the material web takes place point by point line by line and transverse to the longitudinal extent or direction of movement of the material web.

A light receiving device can be arranged in front of or behind the material web depending on whether the fault seeking apparatus operates in reflection (remission) or transmission. It is also possible to use two or more light receiving devices and to monitor both light reflected by, and light transmitted through the web.

The light receiving device generally consists of a cylindrical lens arranged parallel to the path of the scanning light bead generated by the scanning light beam on the web and a light conducting rod arranged behind the cylindrical lens with a photomultiplier at one of the end faces of the light conducting rod.

A further optical system is generally located between the laser and the objective of the ight transmitting device in order to focus the parallel laser beam. The scanning device invariably includes a slot aperture and the objective generally produces an image of this slot in the scanning plane on the surface of the material web.

Structured material such as woven fabrics are generally investigated, in the first instance, in transmission. The surface structure of sheet metal, for example sheet aluminum for use in offset printing, is preferably monitored in remission.

When investigating material webs, in particular textiles such as woven material faults of the most various kinds, such as nap defects, thickened portions, thinner areas, flecks, and breaks in the warp or weft, have to be detected. Dep:nding on the type of fault the nature of the scanning light bead has a considerable influence on the recognition of the fault. If, for example a weft thread is missing in the material then the fault detection is particularly efficient if the scanning light bead has the shape of a slot extending in the scanning direction. A scanning light bead in the form of a slot extending in the transport direction of the web, i.e. at right angles to the scanning direction, is, however, particularly favourable for finding a warp breakage. For customary optical fault seeking apparatus of the kind presently under discussion the monitoring process can, however, only be optimized for the detection of one type of fault.

The principle object underlying the present invention is now to provide optical fault seeking apparatus for material webs of the kind previously named, the response of which can be optimized for the simultaneous detection of very different types of faults. To accomplish this object the invention envisages, in apparatus of the above named kind, that the mirror wheel means has at least first and second alternately operating types of mirror surfaces of which the first projects a first light bead having a first characteristic onto the scanning plane and the second projects a second light bead having a second, different characteristic onto the scanning plane. The first and second characteristics would generally be the size, or the shape, or the size and shape of the first and second light beads.

The thought underlying the invention can thus be seen to be the use of a special mirror wheel which alternately projects, in rapid succession one after the other, into the scanning plane, two different scanning light beads which are rrespectively optimized with respect to their shape and size for the detection of different types of faults. This idea can also be extended by providing the mirror wheel with more than two different types of mirror surfaces in order to achieve a better differentiation during fault recognition.

For use for woven fabrics and in particular for the reliable recognition of both warp and weft breakages a preferred embodiment of the invention envisages that the optical scanning device includes an anamorphotoic lens system, by means of which two slot images extending parallel to the scanning plane and at right angles to one another can be generated, and mirror wheel means with two kinds of mirror surfaces which are preferably alternately operative. In this arrangement one of the two kinds of mirror surfaces projects one of the slot images into the scanning plane and the other projects the other slot image into the scanning plane at right angles to the first slot image. The apparatus is thus optimized for the detection of the faults which prevail in woven fabrics in particular for the recognition of warp and weft thread breakages by arranging for the scanning light bead to be a rapid succession of images of slots alternately extending in, and transverse to, the transport direction of the web. For a weft thread breakage the light receiving device responds in optimized fashion to the transversely disposed slot image, however, for weft thread breakages it is primarily the slot image which extends at right angles to the scanning direction which produces the optimum response of the light receiving device.

One practical embodiment is characterized in that the two slot images are spaced apart in the direction at right angles to the scanning plane and in that the mirror wheel has mirror surfaces of different optical power, which are preferably alternately arranged around the periphery of the mirror wheel. For this purpose the mirror wheel can usefully have plane and curved mirror surfaces in which the curved mirror surfaces are usefully of concave curvature. The curved mirror surfaces can be either of cylindrical or spherical curvature.

A further embodiment features an arrangement in which the mirror wheel means comprises two mirror wheels arranged one adjacent the other with the mirror wheels being displaced by a fraction of a pitch relative to one another in the peripheral direction. Thus two mirror wheels which are identical, apart from any differences in mirror surface construction which may be necessary, are present and are arranged coaxial to one another and preferably directly contact one another.

The two mirror wheels can either have mirror surfaces of different refractive power, by arranging for example for one mirror wheel to have only flat mirror surfaces and the other to have only preferably concave, spherical or cylindrical mirror surfaces, or both mirror wheels can have only plane mirror surfaces and the optical means which cooperate with the two mirror wheels can generate differently shaped and/or dimensioned light beads, in particular two slot images which are at right angles to one another.

In the first embodiment, using mirror surfaces of differential optical power alternately arranged one after the other in the peripheral direction, it is only the mirror wheel which causes the two slot images to be formed in different image planes.

When using a tandem mirror wheel either the differential optical powers of the two mirror wheels or, if their optical powers are the same, the optical means which cooperate with the two mirror wheels can be responsible for ensuring the appearance in the scanning plane of, on the one hand, a slot image extending in the scanning direction and, on the other hand, a slot image extending at right angles to the scanning direction.

Figure 2:
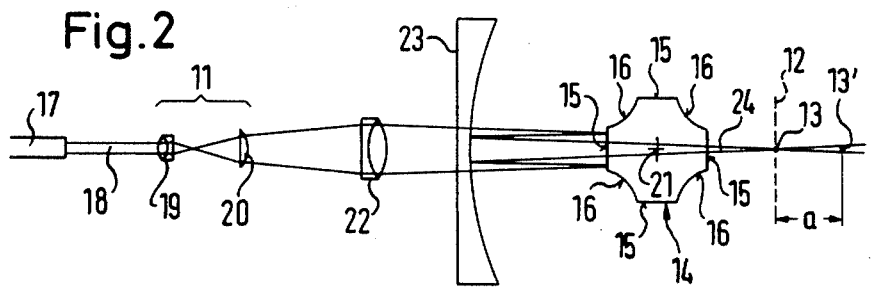
Figure 3:
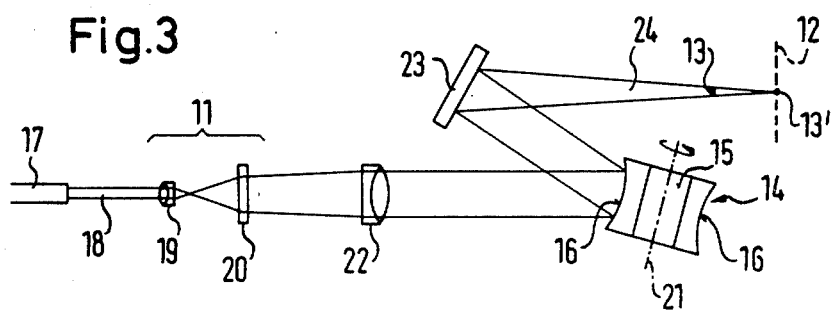
Figure 4:
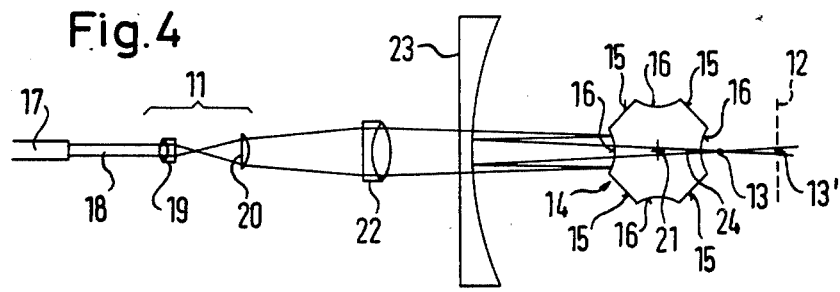

The invention will now be described in further detail and by way of example only with reference to the accompanying drawings in which are shown:

FIG. 1 a schematic plan view of a first embodiment of optical fault seeking apparatus for material webs in accordance with the present invention, FIG. 2 a side view of the subject of FIG. 1, FIG. 3 a plan view corresponding to that of FIG. 1 but showing a mirror wheel rotated by a further mirror surface, FIG. 4 a side view of the subject of FIG. 3

Figure 5:
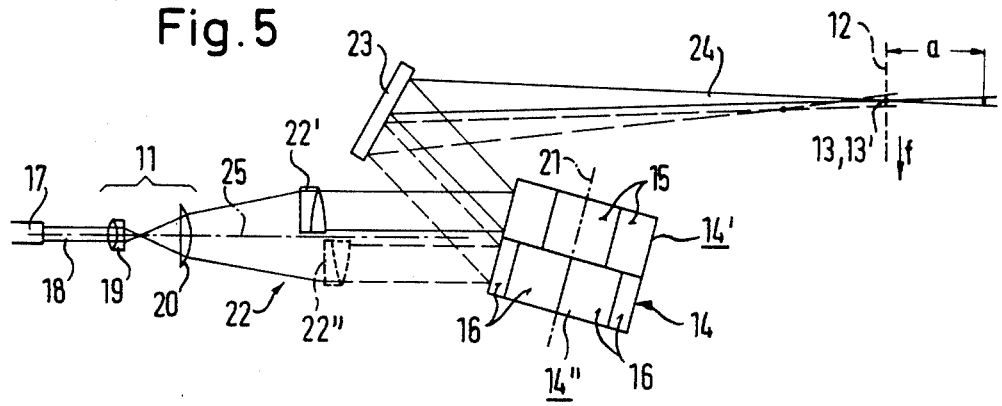
Figure 6:
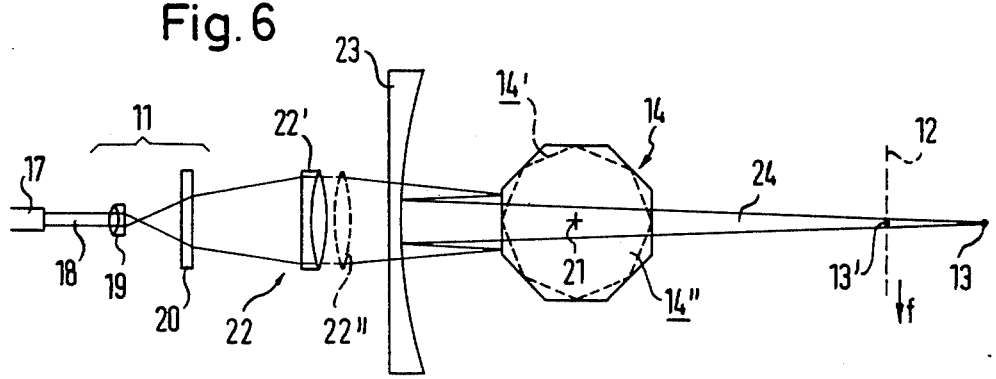
Figure 7:
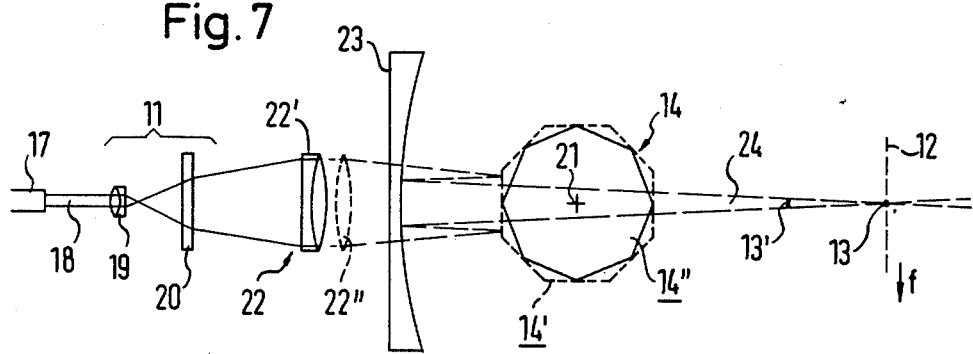

FIG. 5 a plan view of a further embodiment of an optical fault seeking apparatus in accordance with the invention, FIG. 6 a side view of the subject of FIG. 5 in a first position of the associated mirror wheel and FIG. 7 a view similar to the view of FIG. 6 but showing the mirror wheel rotated by a further half pitch.

Referring firstly to FIGS. 1 to 4 a laser 17 transmits a parallel light beam 18 to an anamorphotic lens system 11 which consists of a micro-objective 19 and a cylindrical lens 20 arranged behind the micro-objective 19 with the axis of the cylindrical lens extending substantially parallel to the rotational axis of a mirror wheel 14.

The light beam emerging from the anamorphotic system 11 reaches a strip-like concave mirror 23 via an objective 22 and the mirror surfaces 15, 16 of a mirror wheel 14. The strip-like concave mirror 23 focusses the light beam into the vicinity of the scanning plane 12.

As seen in FIGS. 1 and 2 the axis 21 of the mirror wheel 14 is somewhat tilted relative to the normal to the optical axis of the objective 22 in order to be able to arrange the strip-like concave mirror 23 alongside the light beam which emerges from the objective 22 and to lead the scanning beam 24, which emerges from the concave mirror 23, past the mirror wheel 14. The anamorphotic system 11 together with the objective 22 and the strip-like concave mirror 23 in the plane of FIG. 1 sharply images a gap-like light bead 13 in the scanning plane 12. The scanning direction in FIG. 1 is at right angles to the plane of the drawing. The material web arranged in the scanning plane 12 moves in the direction of the arrow f.

At the same time, by virtue of the operation of the anamorphotic system 11, a slot image 13', which is rotated by 90° and which stands at right angles to the plane of the drawing of FIG. 1, is created at a distance "a" behind the scanning plane 12. In FIG. 2 the longitudinal extent of the slot image 13' can be recognized whilst the first slot image 13 appears as a point.

In accordance with the invention the plane mirror surfaces 15 and the concavely curved mirror surfaces 16 alternate around the periphery of the mirror wheel 14.

To the extent that a plane mirror surface 15 is located, in accordance with FIGS. 1 and 2, in the beam path the slot image 13 which extends in the transport direction f will be focussed in the scanning plane 12.

If now, in accordance with FIGS. 3 and 4, a concavely curved mirror surface 16 is located in the beam path then the slot image 13', which now extends at right angles to the transport direction f, is focussed by the effects of the concave mirror into the scanning plane 12. The other slot image 13 is shifted in front of the scanning plane 12.

During continuous rotation of the mirror wheel 14 slot images 13 and 13', which are alternately rotated through 90°, thus appear in the scanning plane 12.

In the embodiments of FIGS. 5 to 7 the same reference numerals designate items which have corresponding counterparts in FIGS. 1 to 4.

In the embodiments of FIGS. 5 to 7 the mirror wheel 14 is constructed as a tandem mirror wheel with two coaxial mirror wheels 14', 14" which contact one another and which are mutually displaced in the peripheral direction by one half of a mirror surface division, i.e. by one half pitch. The mirror surfaces 15, 16 of the two mirror wheels 14', 14" are plane in the presently described embodiment. The objective 22 is, however, divided in accordance with the invention into two halves 22', 22" so that each of the halves 22', 22" of the objective illuminates one of the mirror wheels 14', 14" respectively. The two objective halves 22', 22" are displaced from one another in the direction of the optical axis 25 by a distance which is sufficient that the so-called intersect difference "a" is balanced out. In other words the slot image 13, and the slot image 13' which extends at right angles thereto, are imaged in the scanning plane 12 by the mirror wheel 14' and the other mirror wheel 14" respectively. At the same time the two partial objectives 22', 22" naturally also image the slot images in front of or behind the scanning plane 12 as is indicated in FIGS. 5 to 7.

Thus the slot images 13, 13' the planes of which are alternately rotated through 90° also arise in this embodiment on rotation of the mirror wheel. FIG. 6 illustrates the image formation by the mirror wheel 14' and the objective half 22' of the slot image 13' which is directed in the transport direction f. FIG. 7 shows the image formation by the mirror wheel 14" and the objective half 22" of the slot image 13 which extends at right angles to the transport direction f.

The arrangement can also be such that one of the two mirror wheels has only plane surfaces whilst the other is constructed only with spherical or cylindrical mirror surfaces. The advantage of this arrangement would be a higher scanning frequency.

If a cylindrical surface is used in place of the spherical mirror wheel surface then one achieves only focussing in a single direction. A point would then be formed from the imaging of the slot. The advantage of this arrangement would be a high fault resolution by the point and on the other hand an optical integration by the slot in the direction of its longitudinal extent. Thus, the mirror wheel means of the invention also means that sharp points and sharp slots can be alternately projected onto the material web. The combination of a sharp image/unsharp image, i.e. for example a smaller point-/larger point or a narrower/wider slot image, can also be realized.

An important feature of the subject of the invention is the fact that the differential characteristics of the light beads in the scanning plane are achieved only with a single light source which is preferably constructed as a laser.

On using two objective halves 22', 22" in accordance with the embodiment of FIGS. 5 to 7 it is also possible to select an arrangement in which, in place of the axial displacement of the two objective halves, each objective half has a different focal length such that for the one focal length the one slot image 13, and for the other focal length the other slot image 13' is sharply imaged in the scanning plane 12.

Thus, in accordance with the invention, each second mirror wheel surface is provided with additional optical power which is achieved in one embodiment by providing every second mirror wheel surface with a spherical profile. Cylindrical surfaces can also be basically used, one then no longer achieves a rotated image but rather the slot image formed via the flat surface is contracted to a point by the effects of the cylindrical curvature.

When using a tandem mirror wheel and a split objective the differential focussing can be achieved by axial displacement or differential focal length of the two parts of the objective.

We claim:

1. Optical fault seeking apparatus for material webs comprising an optical scanning device including mirror wheel means and a light source for projecting beams of light onto a material web moving in a scanning plane of the apparatus to form beads of light thereon and for scanning said beads of light cyclically across the scanning plane transverse to the direction of movement of the material web, at least one light receiving device arranged to pick up light from the light beads formed on the web and to guide this light to at least one associated photoelectric converter for producing an electrical signal corresponding to the light received, and wherein said mirror wheel means has at least first and second alternately operating types of mirror surfaces of which the first projects a first light bead having a first characteristic onto said material web and the second projects a second light bead having a second different characteristic onto said material web.

2. Optical fault seeking apparatus in accordance with claim 1 and wherein said first and second characteristics are the sizes of said first and second light beads.

3. Optical fault seeking apparatus in accordance with claim 1 and wherein said first and second characteristics are the shapes of said first and second light beads.

4. Optical fault seeking apparatus in accordance with claim 1 and wherein said first and second characteristics are the size and shape of said first and second light beads.

5. Optical fault seeking apparatus in accordance with claim 1 and wherein said light source is a laser light source.

6. Optical fault seeking apparatus in accordance with claim 1 wherein said optical scanning device further includes an anamorphotic lens system for generating two slot images extending parallel to the scanning plane and at right angles to one another and wherein said first type of mirror surface projects one of the slot images into the scanning plane and said second type of mirror surface projects the other slot image at right angles to the first slot image into the scanning plane.

7. Optical fault seeking apparatus in accordance with claim 6 wherein the two slot images are separated in the direction at right angles to the scanning plane and wherein said first and second types of mirror surfaces have different optical powers.

8. Optical fault seeking apparatus in accordance with claim 7 and wherein the mirror wheel means have flat and curved mirror surfaces.

9. Optical fault seeking apparatus in accordance with claim 8 and wherein the curved mirror surfaces are of concave curvature.

10. Optical fault seeking apparatus in accordance with claim 8 and wherein the curved mirror surfaces are of cylindrical curvature with the axes of curvature extending parallel to the axis of the mirror wheel means.

11. Optical fault seeking apparatus in accordance with claim 8 and wherein the curved mirror surfaces are spherically curved.

12. Optical fault seeking apparatus in accordance with claim 6 and wherein said mirror wheel means comprises two mirror wheels arranged one adjacent the other with the mirror wheels being displaced by a fraction of a pitch relative to one another in the peripheral direction.

13. Optical fault seeking apparatus in accordance with claim 12 and in which said fraction of a pitch is substantially one half of a pitch.

14. Optical fault seeking apparatus in accordance with claim 12 and wherein said first and second mirror wheels have mirror surfaces of different optical power.

15. Optical fault seeking apparatus in accordance with claim 14 and wherein the one mirror wheel has only plane mirror surfaces, and the other mirror wheel has curved mirror surfaces the curvature of which is chosen from the group consisting of concave, spherical and cylindrical.

16. Optical fault seeking apparatus in accordance with claim 12 wherein the first and second mirror wheels have only plane mirror surfaces and wherein said optical scanning device includes first and second objective elements, said elements cooperating respectively one with each of the first and second mirror wheels whereby both of said slot images are formed in said scanning plane.

17. Optical fault seeking apparatus in accordance with claim 16 and wherein said first and second objective elements comprise first and second objective halves displaced from one another.

18. Optical fault seeking apparatus in accordance with claim 16 and wherein said first and second objective elements comprise first and second objective halves of different focal lengths.

* * * * *